United States Patent [19]

Spehar et al.

[11] Patent Number: 4,753,536
[45] Date of Patent: Jun. 28, 1988

[54] DISPENSING MIXER FOR THE STORAGE AND MIXING OF SEPARATE MATERIALS

[76] Inventors: Edward R. Spehar, 49 Orion Way, Neshanic Station, N.J. 08853; Bernard F. Harkins, 2000 Woodland Ave., S. Plainfield, N.J. 07080; Laurence Colin, Box 301, Cross River, N.Y. 10518

[21] Appl. No.: 23,838

[22] Filed: Mar. 9, 1987

[51] Int. Cl.$^4$ .............................................. B01F 15/02
[52] U.S. Cl. ........................................ 366/339; 366/338; 366/189; 366/194; 222/494
[58] Field of Search ............... 366/184, 189, 194, 195, 366/196, 280, 338, 339; 222/490–494

[56] References Cited

U.S. PATENT DOCUMENTS 3,390,814  7/1968  Creighton et al. .................. 366/130
4,538,920  9/1985  Drake .................................. 366/339

FOREIGN PATENT DOCUMENTS 2467147  5/1981  France .................................. 222/494

Primary Examiner—Harvey C. Hornsby
Assistant Examiner—Steve Gerrity

[57] ABSTRACT

A portable dispensing mixer for intermixing and dispensing two contiguous streams of material in a preset volumetric ratio. The dispensing mixer includes a syringe with two compartments, discharge assembly for discharging material from the syringe and a nozzle assembly for dispensing the discharged material from a common nozzle. The nozzle assembly comprises a common nozzle, a static mixing element with an arm extending from one end and a head. The head has an end stop for stopping rotation of the arm. The mixing element is caused to rotate by the ingress of material fed through the nozzle until the arm hits the end stop.

9 Claims, 3 Drawing Sheets

DISPENSING MIXER FOR THE STORAGE AND MIXING OF SEPARATE MATERIALS

FIELD OF INVENTION

This invention relates to a portable device for intermixing and dispensing two contiguous streams of material in a preset volumetric ratio independent of their relative viscosity.

BACKGROUND

Commercial devices are readily available for intermixing separate materials and dispensing the mixed product through a common spout. The devices vary based upon the composition of the materials to be mixed, their relative viscosity and the application for the intermixed product.

In the dental profession, the practice of combining polymerizable composite materials for use in filling tooth cavities or for forming dental restorations has become commonplace. In the past, polymerizable materials were combined into a homogeneous mass by a hand operation. This practice is not only time consuming but cannot assure their proper proportion. The volumetric proportion of the materials in the mixed product controls its physical properties and the required exposure time to provide adequate curing. Accordingly, mixing the materials automatically permits presetting the volumetric proportion to maximize the physical properties and provides control over the exposure time.

One commercially available device for intermixing two dental restorative resins and discharging the mixed product through a common discharge nozzle is shown and described in U.S. Pat. No. 4,538,920. The intermixing of the resinous material is accomplished by using a static mixing element located in the discharge nozzle. The operation of the static mixing element and the geometrical configuration of its mixing blades is based on earlier prior patent disclosures such as for example U.S. Pat. Nos. 3,286,992 and 3,664,638. In the aforementioned U.S. Pat. No. 4,538,920, the static mixing element is securely held in a fixed position in order to maintain a predetermined alignment of the first blade of the static mixing element relative to the two streams of resinous material. In accordance with the teaching of the patent, a fixed and predetermined alignment of the mixing element in a premixing chamber or exit conduit is necessary to achieve maximum mixing of the two streams of resinous materials in the discharge nozzle. A complex assembly of components is described to accomplish proper rotational alignment of the static mixing element. This complex assembly requires accurate alignment which is labor intensive and is, accordingly, relatively expensive to fabricate.

DISCLOSURE OF THE INVENTION

The device of the present invention also uses a syringe with multiple compartments for storing two separate polymeric materials, a single discharge nozzle and a conventional static mixing device made from a multiplicity of twisted auger-like mixing elements or blades preferably as shown in U.S. Pat. No. 3,704,006. However, in accordance with the design for the dispensing mixer of the present invention, the static mixing element is arbitrarily dropped into the discharge nozzle without establishing any preset or prefixed rotational alignment. Instead, the static mixing element rotates into a fixed position against a stop and remains immobile in the fixed position for as long as material is being fed into the discharge nozzle. This substantially simplifies the manufacture of the device. In addition, the dispensing mixer of the present invention includes a separate diaphragm member for each compartment to prevent leakage between compartments during storage. The diaphragm members are designed to open in response to a predetermined amount of pressure under the control of the operator. Accordingly, the device is simple in design and does not require the static mixing element to be held in a preset rotationally aligned position to assure satisfactory mixing. The volumetric ratio between the two streams of material may be adjusted by varying the size of the syringe compartments.

The present invention relates to the design of a dispensing mixer for intermixing and dispensing at least two materials from a common nozzle compris- ing:

a syringe having at least two compartments for separately storing each of the materials to be intermixed;

discharge means for simultaneously discharging material from each of said compartments;

a diaphragm member located in each compartment at one end thereof for securing the material stored in each compartment respectively with each diaphragm adapted to open in response to a predetermined applied pressure from said discharge means; and a nozzle assembly comprising said common nozzle, with said nozzle having a bore for receiving the materials dispensed from said syringe and a head extending from said nozzle for coupling said nozzle assembly to said syringe, a static mixing element disposed within the bore of said nozzle for intermixing the materials fed to said nozzle, said static mixing element having an arm at one end thereof for engaging an end stop projecting from said head to render said static mixing element immobile in response to the ingress of material fed into said nozzle.

BRIEF DESCRIPTION OF DRAWINGS

The arrangement and configuration which best illustrates the preferred embodiment of the invention is illustrated in the accompanying drawings, which are to be considered as exemplary rather than limiting, and wherein.

DETAILED DESCRIPTION

Figure 1:
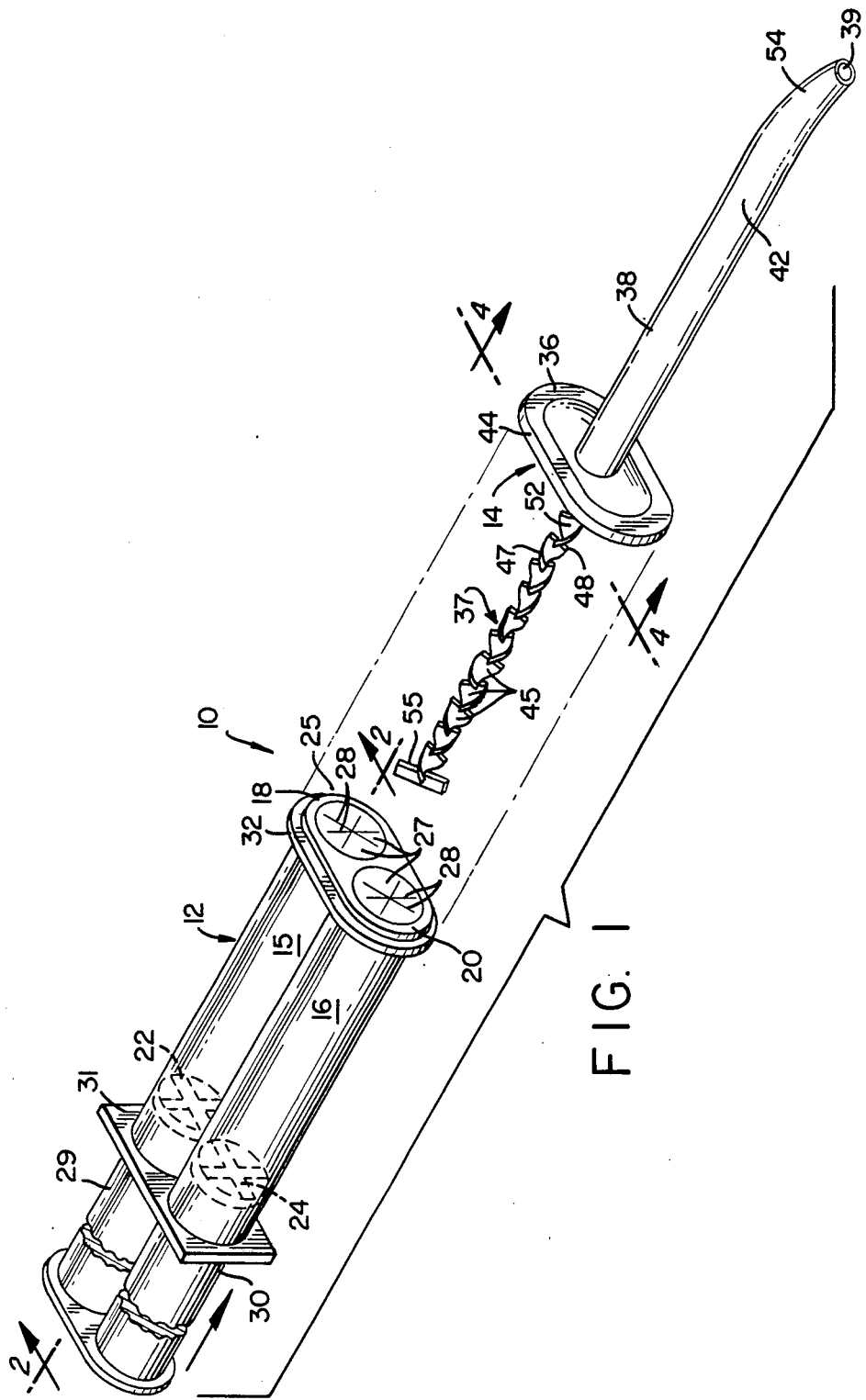
FIG. 1 is an exploded view in perspective of the material storage and dispensing mixer of the present invention.

Referring now to FIG. 1 showing an exploded view in perspective of the dispensing mixer of the present invention. The dispensing mixer is identified by the reference numeral 10 and comprises in combination, a syringe 12 and a nozzle assembly 14. The syringe 12 is formed from any moldable plastic composition preferably polystyrene having two compartments 15 and 16 for separately storing preselected materials to be combined, intermixed and discharged from the nozzle assembly 14. The compartments 15 and 16 may be of any configuration preferably cylindrical and in the embodiment of FIG. 1, are of equal size with each forming a hollow chamber having a predetermined fixed volume. The storage compartments 15 and 16 are adapted to be filled with any material composition of any desired viscosity based on the application for the mixed product.

Each compartment 15 and 16 includes a diaphragm member 18 and 20 and a sealing cap 22 and 24 respectively. The diaphragm members 18 and 20 are in the form of thin cylindrical disks fixedly mounted within the compartments 15 and 16 at the proximal end 25 of the syringe 12. Each diaphragm member 18 and 20 has a plurality of score lines 27 which penetrate through a substantial portion of the thickness of the diaphragm members for forming a multiplicity of pie-shaped sections 28. Upon the application of sufficient pressure, the sections 28 open up to permit the discharge of material from the compartments 15 and 16 past the diaphragm members 18 and 20 into the nozzle assembly 14.

The stored materials are driven simultaneously from the compartments 15 and 16. Any conventional drive mechanism such as a pair of pistons 29 and 30 may be used for this purpose. The pistons 29 and 30 are coupled together to be driven in unison using, e.g., a conventional double barrelled ratchet type caulking gun (not shown), which may be either mechanically or automatically actuated.

The diaphragm members 18 and 20 may be fixedly mounted in each compartment 15 and 16 at the proximal end 25 of the syringe by press fitting each diaphragm member into a compartment and ultrasonically welding it to the compartment or simply by applying an adhesive between the diaphragm members 18 and 20 and the compartment walls. The diaphragm members 18 and 20 should be very thin in order to permit the sections 28 to exhibit a natural resiliency or tendency to self lock and return to its normally closed position after the applied force from the pistons 29 and 30 has been removed. The preferred material for the diaphragm members 18 and 20 is polyethylene although a thin metallic material may equally be used. The self locking nature of the diaphragm members 18 and 20 permits the syringe 12 to be used repeatedly or intermittently without emptying the stored contents of each compartment 15 and 16 during each use. The self locking diaphragm members 18 and 20 effectively reclose each compartment 15 and 16 to prevent any remaining material from intermixing, curing and solidifying.

Figure 2:
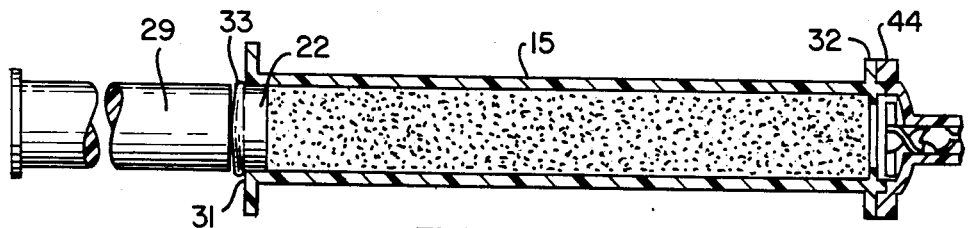
FIG. 2 is a cross sectional view of one of the syringe compartments taken along the lines 2—2 of FIG. 1.
Figure 3:
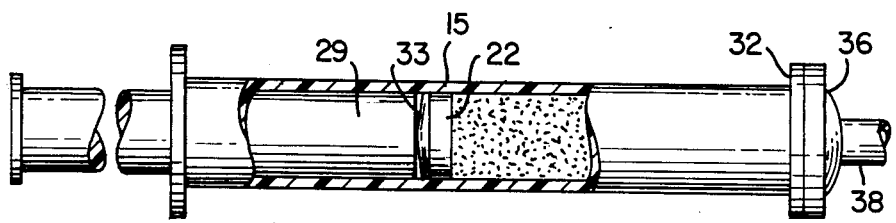
FIG. 3 is a cross sectional view similar to FIG. 2 showing the syringe of FIG. 2 in a partially discharged position.

The sealing caps 22 and 24 are removably inserted into the compartments 15 and 16 at the distal end 31 of the syringe 12 after each of the compartments 15 and 16 is filled with a desired material composition. Each sealing cap 22 and 24 has a resilient annular shoulder 33 as best shown in FIGS. 2 and 3 which is located about its periphery to permit the sealing caps 22 and 24 to seal the compartments and to slidably move along the chamber walls of the compartments 15 and 16 in response to a corresponding movement of the pistons 29 and 30. The annular shoulder 33 prevents backflow of material while the pistons 29 and 30 are advancing.

Figure 4:
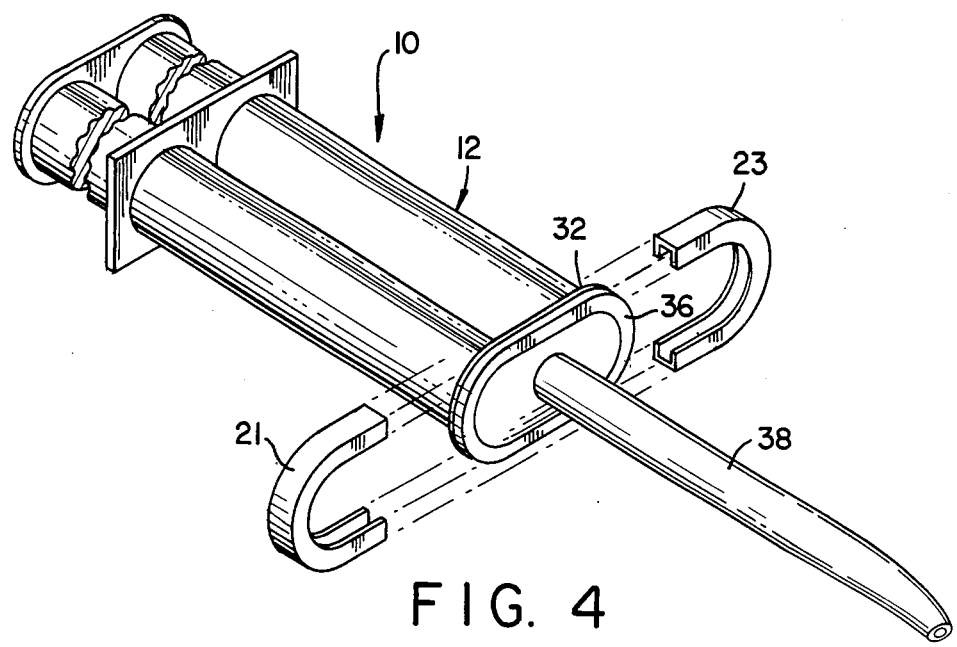
FIG. 4 is a view in perspective of the material storage and dispensing mixer of FIG. 1 in combination with locking means for securing the head of the nozzle assembly to the syringe.
Figure 5:
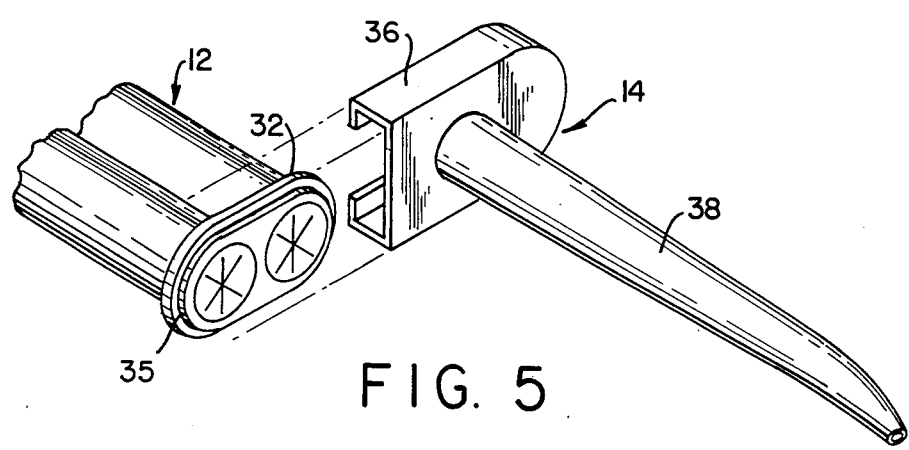
FIG. 5 shows an alternate embodiment using a detachable clamp like head on the nozzle for securing the nozzle assembly of the mixer to the syringe.

A collar 32 is molded about the body of the syringe 12 for coupling the syringe 12 to the nozzle assembly 14. The collar 32 is recessed from the proximal end 25 of the syringe 12 to form a ledge 35 which is slidably inserted into the head 36 of the nozzle assembly 14 with the collar 32 abutting a rim 44 extending from the head 36. The rim 44 may be either permanently affixed to the collar 32 or mechanically secured thereto. A permanent connection may be made by ultrasonically welding the abutting ends together or by bonding the ends using an adhesive. Alternatively, horseshoe clamps 21 and 23 as shown in FIG. 4 may be used to clamp the head 36 to the collar 32 to form a mechanical connection which will prevent separation as material is being discharged from the mixer 10. When the syringe 12 is permanently affixed to the nozzle assembly 14 the dispensing mixer 10 is intended to be disposable and thrown away upon exhausting the supply of stored material in the syringe 12. With the syringe 12 mechanically interlocked to the nozzle assembly 14, the nozzle assembly 14 may be reused and a different syringe 12 substituted for the spent one. An alternative embodiment for mechanically interconnecting the nozzle head 36 to the collar 32 is shown in FIG. 5. The head 36 is formed in the shape of a "C" type clamp which functions as a bracket for slidably engaging and securing the collar 32 within the nozzle head 36. This permits the nozzle assembly 14 to be readily disconnected from the syringe 12 after use, and reconnected to a new syringe.

The nozzle assembly 14 further includes a static mixer 37 and a nozzle 38 which extends axially outwardly and then tapers down to a discharge opening 39. The nozzle 38 has a central bore 42 which extends axially from the head 36 to the distal end 54 at the nozzle 38. The head 36 of the nozzle assembly 14 has a depressed area 40 which forms a marginal well into which material may flow and merge before entering into the bore 42 of the nozzle 38.

The static mixer 37 of the nozzle assembly 14 consists of a multiple number of serially arranged blades 45 which have a bow tie like configuration. Each blade 45 is twisted so that its upstream and downstream edges 47 and 48 respectively are at a substantial angle to each other and with each adjacent successive blade 45 twisted in an opposite direction with respect to its preceding blade. It is now well known that if a static mixer 37 is held in a stationary position in a nozzle it will cause substantial intermixing of any two component fluids when forced through such nozzle.

The static mixer 37 is arbitrarily inserted into the bore 42 of the nozzle 38 so that its forward blade 52 will nestle against the distal end 54 of the nozzle 38. The static mixer 39 has an arm 55 extending from the rearward end thereof which lies substantially transverse to the longitudinal axis of the nozzle 38.

Figure 6:
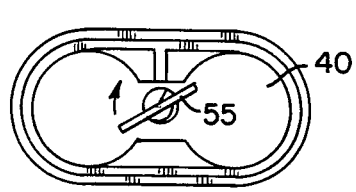
FIG. 6 is a view from the rear of the nozzle assembly of the mixer of FIG. 1 taken along the lines 4—4 showing the static mixing device in its assembled position in the nozzle assembly prior to use of the mixer.
Figure 7:
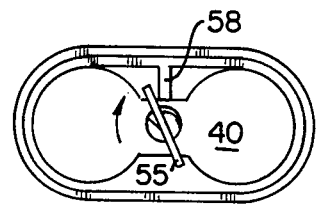
FIG. 7 is another view similar to FIG. 4 showing the static mixing device rotated into a locked position in response to the ingress of storage material fed from the syringe.

The static mixer 37 is rotated into a fixed position from any initial arbitrary position as is depicted in FIGS. 6 and 7. The position shown in FIG. 6 represents an arbitrary placement of the static mixer 37 in the nozzle 38. The discharge of material from compartments 15 and 16 of the syringe 12 causes the static mixer to turn until the arm 55 engages the end stop 58 as shown in FIG. 7. This occurs almost immediately following the ingress of the storage materials into the nozzle 38. The end stop 58 prevents further rotation of the arm 55 as material is fed into the nozzle 38 thereby allowing the mixer to intermix the two materials from the separate storage compartments 15 and 16.

A turning force is initiated to rotate the static mixer 37 due to the geometrical configuration of the serially arranged blades 45 extending from the static mixer 37. However, once the static mixer 37 is rendered immobile the materials fed through the mixer 37 intermix to form a relatively homogeneously mixed product.

Figure 8:
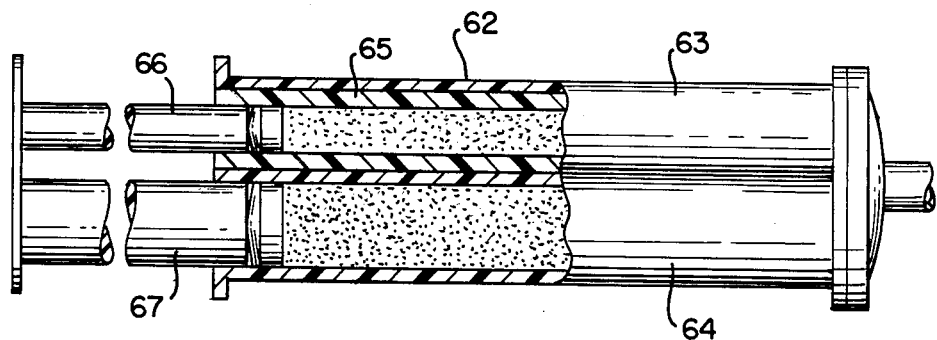
FIG. 8 shows an alternate embodiment of the syringe of FIG. 1.

Since the compartments 15 and 16 in the syringe 12 of FIG. 1 are of equal size and the pistons 29 and 30 move in unison the volume of material displaced in each compartment 15 and 16 will be equal independent of the material viscosity and independent of any difference in viscosity. In the embodiment of FIG. 8 a syringe 62 is shown corresponding to the syringe 12 of FIG. 1 except that the compartments 63 and 64 are of unequal diameter. This can be accomplished by changing the diameter of the compartment 63 relative to the compartment 64 using for example a removable liner 65. This changes the mixing ratio of the materials discharged from the compartments 63 and 64 respectively. The pistons 66 and 67 must, however, also be sized corresponding to the selected diameters for the compartments 63 and 64. The use of different volumes for the compartments provides control over the volumetric ratio of discharged material from the syringe 62.

The discharge opening 39 of the nozzle 38 may be varied using a closed taper which the operator can snip off to control the size of the discharge opening 39.

Various modifications and alterations of this invention will be apparent to those skilled in the art without departing from the scope and spirit of this invention and the latter should not be restricted to that set forth herein for illustrative purposes.

What is claimed is:

1. A dispensing mixer for storing, intermixing and dispensing at least two materials from a common nozzle comprising:
   a syringe having at least two compartments for separately storing each of the materials to be intermixed;
   discharge means for simultaneously discharging material from each of said compartments;
   a diaphragm member located in each compartment at one end thereof for securing the material stored in each compartment respectively with each diaphragm adapted to open in response to a predetermined applied pressure from said discharge means; and
   a nozzle assembly comprising said common nozzle with said nozzle having an inlet end, an outlet end and a bore extending from said inlet end to said outlet end for receiving the materials dispensed from said syringe, a head extending from said nozzle for coupling said nozzle assembly to said syringe, an end stop projecting from said head; a static mixing element disposed in arbitrary alignment within the bore of said nozzle relative to said syringe for intermixing the materials fed to said nozzle, with said static mixing element including a multiple number of serially connected blades and having an arm extending from one end of said serially connected blades for engaging said end stop to render said static mixer immobile in response to the ingress of material fed through said nozzle.

2. A dispensing mixer as claimed in claim 1 wherein said head extends from the inlet end of the nozzle and wherein said arm extends from said static mixing element adjacent the inlet end of the nozzle.

3. a dispensing mixer as defined in claim 2 wherein each diaphragm member has a multiple number of sections which open in response to pressure from said discharge means and close upon the removal of pressure to self lock each compartment.

4. A dispensing mixer as defined in claim 3 wherein said syringe has a collar for engaging said head to couple said nozzle assembly to said syringe.

5. A dispensing mixer as defined in claim 4 wherein said collar is permanently secured to said head to form a disposable mixer adapted to be thrown away upon discharging the contents from each compartment.

6. A dispensing mixer as defined in claim 4 wherein said collar is detachably coupled to said head.

7. A dispensing mixer as defined in claim 6 wherein said head is in the form of a clamp for removably engaging the collar from said syringe.

8. A dispensing mixer as defined in claim 6 further comprising a sealing cap for each compartment with each sealing cap having an annular shoulder for slidably moving within each chamber in response to the movement of said discharge means.

9. A dispensing mixer as defined in claim 8 further comprising means for changeing the mixing ratio between the materials from each compartment.

* * * * *